United States Patent
Canessa et al.

(10) Patent No.: US 7,933,472 B1
(45) Date of Patent: Apr. 26, 2011

(54) SYSTEM FOR REMOTELY GENERATING AND DISTRIBUTING DICOM-COMPLIANT MEDIA VOLUMES

(75) Inventors: John C. Canessa, Apple Valley, MN (US); Giancarlo Canessa, Eagan, MN (US); Gino Canessa, Eagan, MN (US)

(73) Assignee: Datcard Systems, Inc., Irvine, CA (US)

( * ) Notice: Subject to any disclaimer, the term of this patent is extended or adjusted under 35 U.S.C. 154(b) by 948 days.

(21) Appl. No.: 11/740,062

(22) Filed: Apr. 25, 2007

Related U.S. Application Data

(60) Provisional application No. 60/795,141, filed on Apr. 26, 2006.

(51) Int. Cl.
G06K 9/54 (2006.01)
G06Q 10/00 (2006.01)
(52) U.S. Cl. .......................................... 382/305; 705/11
(58) Field of Classification Search .................. 382/128, 382/132, 305; 705/2, 3, 4, 1.1
See application file for complete search history.

(56) References Cited

U.S. PATENT DOCUMENTS

| | | | |
|---|---|---|---|
| 5,592,511 A | 1/1997 | Schoen et al. | |
| 5,633,839 A | 5/1997 | Alexander et al. | |
| 5,740,134 A | 4/1998 | Peterson | |
| 5,920,317 A | 7/1999 | McDonald | |
| 5,974,004 A | 10/1999 | Dockes et al. | |
| 6,188,782 B1 | 2/2001 | LeBeux | |
| 6,241,668 B1 | 6/2001 | Herzog | |
| 6,529,757 B1 | 3/2003 | Patel et al. | |
| 6,574,629 B1 | 6/2003 | Cooke et al. | |
| 6,678,703 B2 * | 1/2004 | Rothschild et al. | 1/1 |
| 6,678,764 B2 | 1/2004 | Parvulescu et al. | |
| 6,772,026 B2 * | 8/2004 | Bradbury et al. | 700/98 |
| 6,910,038 B1 | 6/2005 | James | |
| 7,120,644 B1 | 10/2006 | Canessa | |
| 2002/0085476 A1 | 7/2002 | Samari-Kermani | |
| 2004/0215637 A1 | 10/2004 | Kitamura et al. | |
| 2005/0102170 A1 * | 5/2005 | Lefever et al. | 705/4 |
| 2007/0272747 A1 * | 11/2007 | Woods et al. | 235/385 |

* cited by examiner

*Primary Examiner* — Yon Couso
(74) *Attorney, Agent, or Firm* — Knobbe, Martens, Olson & Bear LLP

(57) ABSTRACT

A system for generating digital image media volumes includes a digital image terminal for receiving, processing, and transmitting digital image data, and being adapted for processing the digital image data into one or more discrete DICOM-standard data objects. The system further includes a media volume production facility remotely located from the digital image terminal, and communicatively coupled to the digital image terminal via a server-operated computer network.

16 Claims, 2 Drawing Sheets

SYSTEM FOR REMOTELY GENERATING AND DISTRIBUTING DICOM-COMPLIANT MEDIA VOLUMES

CROSS-REFERENCE TO RELATED APPLICATIONS

This application claims priority to U.S. Provisional Patent Application Ser. No. 60/795,141, filed on Apr. 26, 2006, and entitled "SYSTEM FOR REMOTELY GENERATING AND DISTRIBUTING DICOM-COMPLIANT MEDIA VOLUMES", the content of which is incorporated herein in its entirety.

FIELD OF THE INVENTION

The present invention relates to systems for generating and distributing media volumes containing digital image data, and more particularly to systems for remotely generating and distributing digital image data-recorded media volumes through electronically-transmitted commands.

BACKGROUND OF THE INVENTION

Modern healthcare facilities now regularly utilize digital imaging modalities such as magnetic resonance (MR), computer tomography (CT), digital radiography, and ultrasound devices. These modalities, referred to as input imaging devices, produce vast numbers of diagnostic quality digital medical images. In order to more easily manage and distribute such digital images, many healthcare facilities rely upon compact recordable media, such as optically-recordable compact discs (CD) and digital video discs (DVD).

A formatting standard that is commonly used in the healthcare industry for recording such digital image data is the Diagnostic Imaging and Communications in Medicine (DICOM) standard. Through such a format, electronic data supporting digital images are recorded onto recordable media volumes as DICOM objects. The generation and recordation of such DICOM objects requires specific dedicated equipment, hardware, and software. While many facilities operate their own DICOM-compliant volume generation systems, some facilities find that owning, maintaining, and operating their own systems is expensive, and other facilities do not have the demand to justify owning, maintaining, and operating their own equipment. As such, there is a need in the art for systems that are capable of remotely receiving data and instruction from a healthcare facility to generate and distribute DICOM-compliant data object media volumes.

It is therefore a principal object of the present invention to provide a network-based system for receiving digital image data and instructions, and for generating DICOM-compliant media volumes comprising such digital image data, and automatically distributing such recorded media volumes to desired recipients.

It is a further object of the present invention to provide a network-based system for remotely generating and distributing DICOM-compliant media volumes containing user-specified sets of digital image data.

It is a further object of the present invention to provide an automated system which enables remote generation of digital image data-containing media volumes in a DICOM-compliant format, and for automatically labeling and shipping such media volumes to one or more desired recipients, while further automatically invoicing the requesting user.

SUMMARY OF THE INVENTION

By means of the present invention, media volumes containing digital image data, such as that captured from medical imaging modalities, may be generated at a site remote from the facility employing the imaging equipment. The recorded media volumes, which are typically used for medical information records, diagnoses, and the like, may be generated through the instruction and direction of personnel located remote from the media volume recording equipment. Specifically, the system and method of the present invention enables computer network access and control of remote digital image recording equipment.

In a particular embodiment, the system for generating digital image media volumes includes a digital image terminal for receiving, processing, and transmitting digital image data, with the digital image terminal being adapted for processing the digital image data into one or more discrete DICOM-standard data objects. The system preferably further includes a media volume production facility remotely located from the digital image terminal, and communicatively coupled to the digital image terminal via a server-operated computer network. The media volume production facility includes a data recorder device for operably recording the DICOM-standard data objects to the digital image media volumes.

In some embodiments, the DICOM-standard data objects further include cataloging data relevant to the respective digital image data. Such cataloging data may include patient study information, patient series information, patient personal information, digital image attributes, and combinations thereof.

The media volume production facility may further include a shipping label printer for printing shipping labels containing shipment recipient information that is parsed from the cataloging data and is transmitted to the shipping label printer from the server.

The media volume production facility may also include a packaging station for automatically affixing the shipping labels to packaging containing one or more respective digital image media volumes.

The system may also include an invoicing module for automatically generating and transmitting invoices to a digital media volume ordering entity upon receipt of a digital media volume order at the server.

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figure which is intended to be representative of various embodiments of the invention. Other embodiments and aspects of the invention are recognized as being within the grasp of those having ordinary skill in the art.

Figure 1:
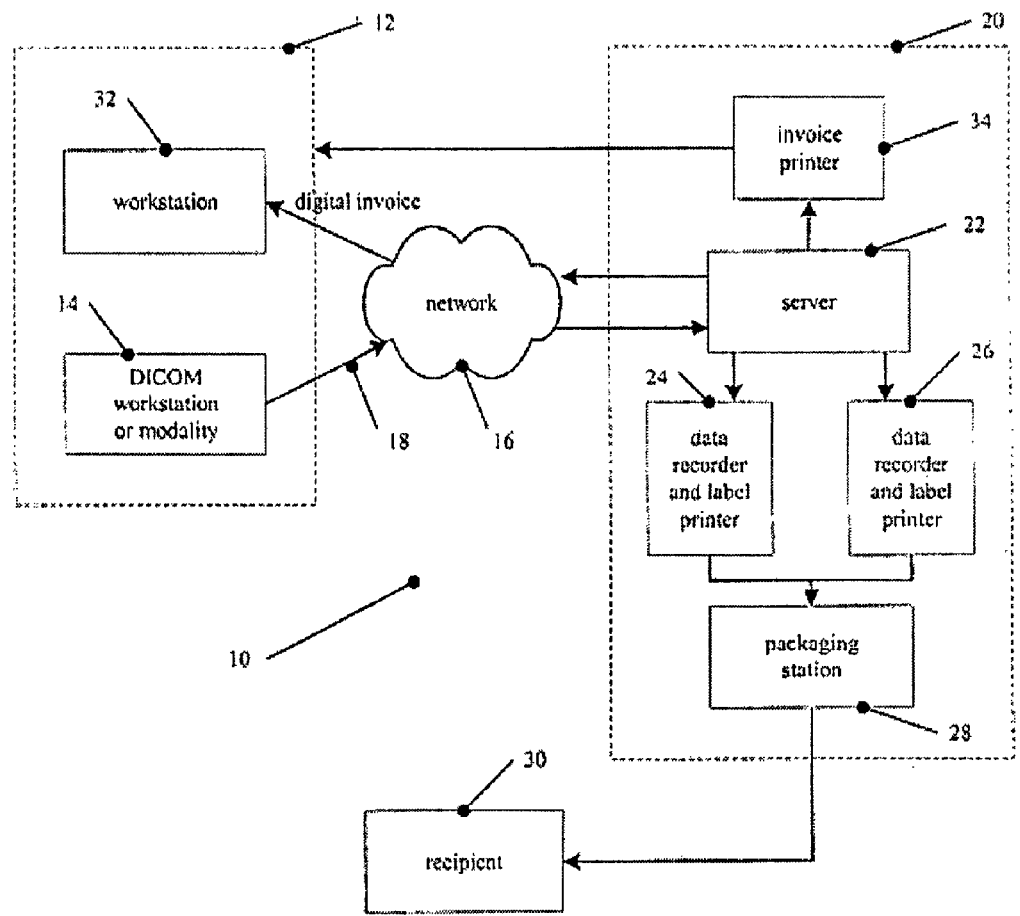
FIG. 1 is a schematic diagram of the system of the present invention.

With reference now to FIG. 1, system 10 of the present invention involves a healthcare facility schematically illustrated at 12, which healthcare facility 12 includes one or more DICOM terminals 14 that receive and collate digital image data from a variety of digital image modalities utilized at healthcare facility 12. In preferred embodiments, DICOM terminal 14 is configured for processing the digital image data in a DICOM-compliant format, so as to generate DICOM-standard objects representing the digital images received from various sources within healthcare facility 12.

In preferred embodiments of the present invention, the one or more DICOM terminals 14 are operably coupled to a network 16 through a network connection 18. Network 16 may be one or more of a variety of network types, such as local area networks (LAN) such as intranets, wide area networks (WAN) such as a global communication network (Internet), and the like. Connection to such network 16 may be accomplished through a variety of network connection types, and through various communication protocols. Examples include Ethernet, DSL, Cable, radio frequency, and other wired or wireless connections. In some embodiments, the use of an application, plug-in and/or a web browser may be required in allowing DICOM terminal 14 to communicate and submit data objects outside of a DICOM network. Accordingly, such application, plug-in, or web browser may be an additional feature required at DICOM terminal 14 for communication to network 16, as illustrated in FIG. 1. Preferably, network connection 18 is suitable for transmitting raw digital image data and/or DICOM-standard objects representing such digital images and relevant cataloging information.

Preferably, network 16 is further communicatively coupled to remote media volume production facility 20, and particularly to a server 22 that is located at, or in communication with facility 20. Although facility 20 is illustrated in FIG. 1 as being contained in a single location, it is contemplated by the present invention that such facility 20 may be distributed among a variety of distinct locations. Specifically, facility 20 need only represent a theoretical grouping of one or more of the components illustrated as being contained with facility 20.

Server 22 preferably receives electronic image data from DICOM terminal 14 through network 16. As described above, such electronic image data may be in the form of DICOM-formatted data objects. In addition to the image data itself, the DICOM objects may further include cataloging data relevant to the image data. This cataloging data includes, for example, patient information, study and series information, date of image, healthcare facility, recipient information, and the like. The DICOM objects preferably include a hierarchy beginning with the patient having one or more studies, with each study including one or more series. Each series identified in each study includes one or more discrete image data files. For example, a particular patient may have one study conducted by digital radiography (DR), and another study by ultrasound (US). If that patient has had two separate visits to the healthcare facility wherein images of both types described above were obtained, each visit will comprise a series of the respective study. Moreover, each series may involve a plurality of images defined by a plurality of image data files which are obtained at the visit for each imaging modality.

DICOM terminal 14 may preferably utilize a plug-in module that is specifically configured to create and submit orders to server 22 in conformity with predetermined guidelines. Such a module permits any digital image creating source to utilize the service of the present invention without having to separately provide appropriate software.

The digital image data and the cataloging data may then be utilized by server 22 to direct data recorder device 24 to record DICOM-compliant data objects onto one or more media volumes, with such media volumes typically comprising optically-recordable compact discs, digital video discs, blue-ray discs, and the like. A variety of devices may be utilized data recorded device 24, such as compact disc recorders, digital video disc recorders, and the like. Such recording equipment is commonly referred to as "burners" and utilize laser energy to scribe an optically-readable pattern in the relevant media (CDs, DVDs, etc.). A particular system that may be useful in recording DICOM-compliant data objects onto one or more media volumes is described in U.S. Pat. No. 7,120,644, herein incorporated by references. Moreover, server 22 is preferably programmed to transmit at least certain of the cataloging data received from DICOM terminal 14 to a shipping label printer 26 for generation of one or more shipping labels that reflect the desired recipient of the recorded media volumes generated by data recorder 24. Such recipients are preferably identified at healthcare facility 12 and transmitted to facility 20 via network 16 in the cataloging data associated with the respective DICOM object(s).

In preferred embodiments, the one or more recorded media volumes contain digital image data recorded in a DICOM part 10 format for DICOM 3.0 objects. In some embodiments, each of such recorded media volumes further include a DICOM directory, and optionally one or more DICOM viewers. Preferably, each recorded media volume is labeled on its surface in data recorder device 24 through conventional mechanisms.

The one or more recorded media volumes pertinent to a particular order from healthcare facility 12 is then packaged at packaging station 28, including the affixation to the packaging of the shipping label generated at shipping label printer 26. Such packaged media volumes are then shipped to the appropriate recipient 30.

As a further feature of system 10 of the present invention, server 22 is preferably programmed to transmit invoices for the relevant orders received from healthcare facility 12 through one or both of electronic transmission and/or hardcopy transmission. As shown in FIG. 1, electronic transmission is preferably accomplished through network 16 in a similar fashion as the data receipt described above. Such electronic invoices are preferably received by a work station 32 at healthcare facility 12. In some embodiments, server 22 transmits electronic data to an invoice printer 34, which generates a hardcopy invoice, with such hardcopy invoices being subsequently shipped to healthcare facility 12.

Figure 2:
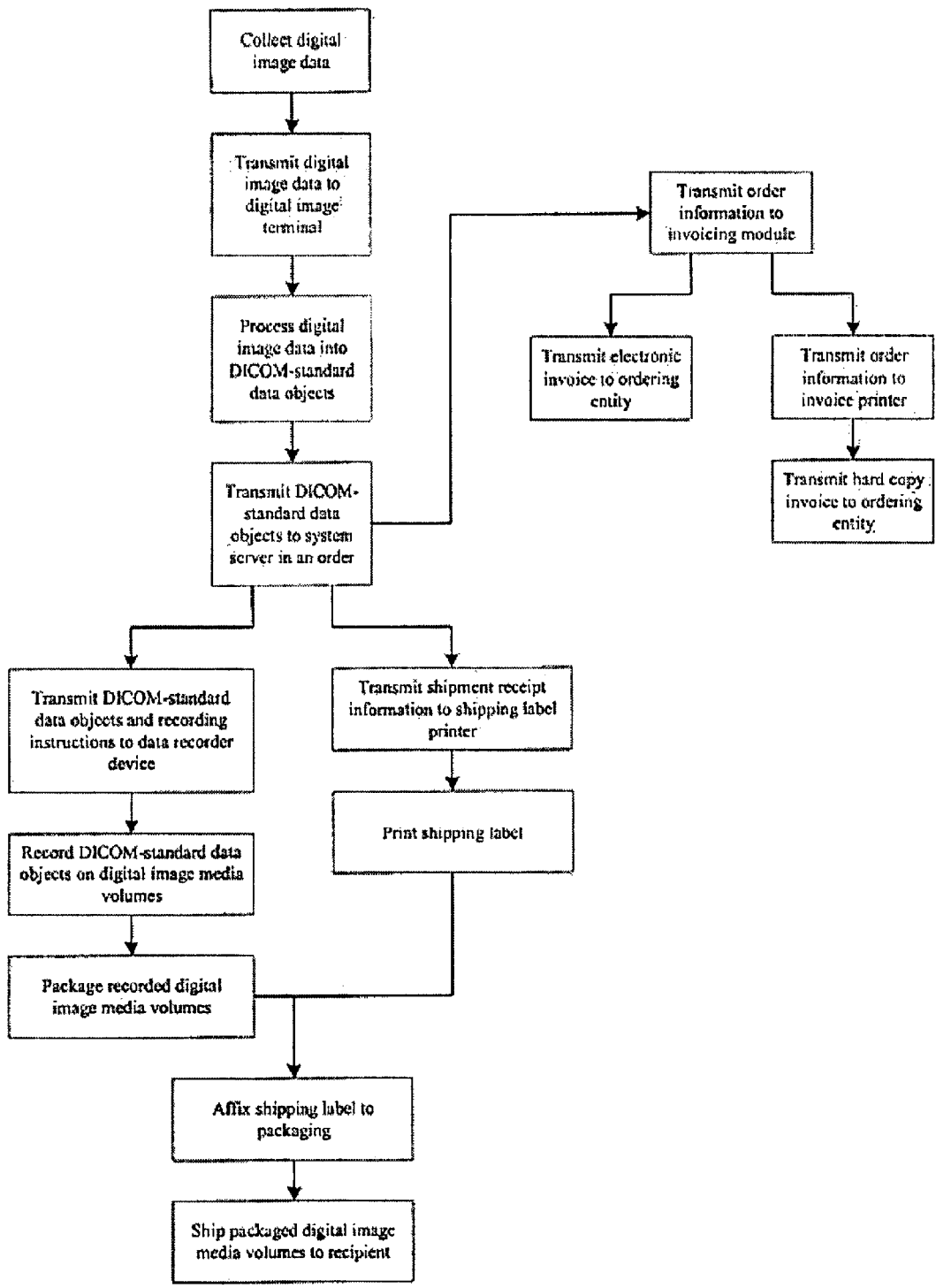
FIG. 2 is a flow diagram demonstrating a method of the present invention.

As demonstrated in the flow diagram of FIG. 2, a method of the present invention involves collecting digital image data on one or more of a variety of digital image capturing modalities, and transmitting such digital image data to a digital image terminal. The raw digital image data is preferably converted or processed into DICOM-standard data objects that each embody one or more discrete digital images. In some embodiments, digital image terminal 14 may include software that is specifically programmed to process raw digital image data into DICOM-standard data objects. An example of such software is eFilm, available from MERGE Healthcare of Milwaukee, Wis. Accordingly, digital image terminal 14 may include digital processing means and software necessary to perform the processing of raw digital image data collected from the various medical imaging modalities into DICOM-standard data objects.

In some embodiments, the DICOM-standard data objects created at digital image terminal 14 are transmitted to a system server 22 in the form of a digital image media volume order. Such an order may include raw digital image data instead of, or in addition to, DICOM-standard data objects containing such raw digital image data. The order transmitted to system server 22 preferably includes attributes for defining instructions in recording the DICOM-standard data objects on one or more digital image media volumes. Such attributes are therefore transmitted in connection with the DICOM-standard data objects to the data recorder device for generation threat of one or more digital image media volumes containing such DICOM-standard data objects.

The attributes associated with the DICOM-standard data objects preferably further include shipment recipient information correlating to the digital image media volumes to be generated. Such shipment recipient information is accordingly transmitted to a shipping label printer for generation of shipping labels thereat. The printed shipping labels may be automatically affixed to the recorded digital image media volume packaging at packaging station 28, and placed in shipment to the intended recipient.

The order attributes transmitted to system server 22 are also preferably forwarded to an invoicing module at system server 22 for generation of appropriate invoices. In some cases, the invoicing module of system server 22 generates an electronic invoice based upon the order attributes, and transmits such electronic invoice to the ordering entity via network 16. In other embodiments, the invoicing module may instead or additionally transmit the order information to an invoice printer 34, where the hardcopy invoice is generated and prepared for delivery to the ordering entity.

The system described above provides a digital image recording system that remotely generates recorded media volumes for shipment to desired recipients, such as referring physicians or patients. The system of the present invention enables healthcare facilities to obtain and generate such recorded media volumes without the necessity of owning, maintaining, and operating the componentry, as contained in facility 20. As such, significant cost savings are realized by the healthcare facilities.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different methods/devices and that various modifications can be accomplished without departing from the scope of the invention itself.

What is claimed is:

1. A system for generating digital media volumes for distribution to a recipient, the system comprising:
    a computer-implemented interface configured to receive an order to produce a digital media volume containing a user-specified DICOM-standard digital image or set of images for distribution to a recipient;
    one or more modalities configured to digitally capture medical data;
    a processor communicatively coupled to the one or more modalities via a computer connection or network, the processor being configured to access the medical data from the one or more modalities and process the medical data into DICOM-standard digital images and cataloging data associated with the digital images;
    a server communicatively coupled to the processor and to the computer-implemented interface via a computer connection or network, the server being configured to receive the order from the interface and access from the processor the specified DICOM-standard digital image(s) and cataloging data associated with the image(s), based on the order;
    a data recorder device remotely located from the processor, and communicatively coupled to the server via a computer connection or network, the data recorder device being configured to receive the specified DICOM-standard digital image(s) from the server and record the DICOM-standard digital image(s) to a portable digital media volume that is removable from the data recorder device for distribution to the recipient; and
    a label printer communicatively coupled to the server via a computer connection or network, the printer being configured to receive the cataloging data from the server and print a shipping label for the digital media volume based on information regarding the recipient parsed from the cataloging data,
    wherein the server comprises an invoicing module configured to generate invoicing data using attributes of the order and transmit the invoicing data to an invoice printer or to the user, based on the creation of the portable digital media volume by the data recorder device.

2. The system of claim 1, wherein the digital media volume is a optically-recordable compact disc (CD) or digital video disc (DVD).

3. The system of claim 1, wherein the cataloging data comprises patient study information, patient series information, patient personal information, and/or digital image attributes.

4. The system of claim 1, further comprising a packaging station associated with the printer that is configured to automatically affix the shipping label to packaging containing the recorded digital media volume.

5. The system of claim 1, wherein the invoice printer is configured to produce a hardcopy invoice based on the invoice data.

6. The system of claim 1, wherein the data recorder device is remotely located from the interface.

7. A system for generating digital media volumes comprising:
    an interface configured to receive from a user an order to produce a digital media volume containing a specified DICOM-standard file or set of files for distribution to a recipient;
    a terminal configured to store DICOM-standard files;
    a server communicatively coupled to the terminal and to the interface via a computer connection or network, the server being configured to receive the order from the interface and access from the terminal the specified DICOM-standard file(s) and cataloging data associated with the file(s), based on the order;
    a data recorder device remotely located from the terminal, and communicatively coupled to the server via a computer connection or network, the data recorder device being configured to receive the specified DICOM-standard files(s) from the server and record the DICOM-standard files(s) to a portable digital media volume that is removable from the data recorder device for distribution to the recipient; and
    an invoicing module coupled to the server via a computer connection or network, configured to generate invoicing data using attributes of the order and transmit the invoicing data to an invoice printer or to the user, based on the creation of the portable digital media volume by the data recorder device.

8. The system of claim 6, wherein the digital media volume is a optically-recordable compact disc (CD) or digital video disc (DVD).

9. The system of claim 6, wherein the invoice printer is configured to produce a hardcopy invoice based on the invoice data.

10. The system of claim 6, wherein the data recorder device is remotely located from the interface.

11. The system of claim 6, wherein the terminal is further configured to store cataloging data associated with the files, and wherein the system further comprises a label printer communicatively coupled to the server via a computer connection or network, the label printer being configured to receive the cataloging data from the terminal and print a shipping label for the digital media volume based on information regarding the recipient parsed from the cataloging data.

12. The system of claim 11, wherein the cataloging data comprises patient study information, patient series information, patient personal information, and/or digital image attributes.

13. The system of claim 11, further comprising a packaging station associated with the label printer that is configured to automatically affix the shipping label to packaging containing the recorded digital media volume.

14. A computer-implemented method for generating digital media volumes comprising:

receiving from a computer-implemented interface an order to produce a digital media volume containing a user-specified DICOM-standard file or set of files for distribution to a recipient;

locating the specified DICOM-standing file(s) and other textual data associated with the file(s) in at least one computer terminal, based on the order;

at a data recorder device, generating a digital media volume that is removable from the data recorder device, the digital media volume containing the specified DICOM-standard files(s);

with a label printer, receiving the cataloging data from the server and printing a shipping label for the digital media volume based on information regarding the recipient parsed from the cataloging data; and generating invoicing data using attributes of the order and transmit the invoicing data to an invoice printer or to the user, based on the creation of the portable digital media volume by the data recorder device.

15. The method of claim 14, further comprising automatically affixing the shipping label to packaging containing the recorded digital media volume.

16. The method of claim 14, wherein the invoice printer is configured to produce a hardcopy invoice based on the invoice data.

* * * * *